US012805827B2

(12) United States Patent
Rong et al.

(10) Patent No.: US 12,805,827 B2
(45) Date of Patent: Nov. 24, 2026

(54) RADAR STETHOSCOPE SYSTEM AND METHOD FOR RESPIRATION AND HEART SOUND ASSESSMENT

(71) Applicant: Arizona Board of Regents on behalf of Arizona State University, Scottsdale, AZ (US)

(72) Inventors: Yu Rong, Tempe, AZ (US); Arindam Dutta, Tempe, AZ (US); Richard Gutierrez, Mesa, AZ (US); Daniel W. Bliss, Phoenix, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 149 days.

(21) Appl. No.: 18/839,896

(22) PCT Filed: Feb. 24, 2023

(86) PCT No.: PCT/US2023/013778
§ 371 (c)(1),
(2) Date: Aug. 20, 2024

(87) PCT Pub. No.: WO2023/164102
PCT Pub. Date: Aug. 31, 2023

(65) Prior Publication Data

US 2025/0152122 A1 May 15, 2025

Related U.S. Application Data

(60) Provisional application No. 63/313,971, filed on Feb. 25, 2022.

(51) Int. Cl.
*A61B 7/04* (2006.01)
*A61B 5/00* (2006.01)
(Continued)

(52) U.S. Cl.
CPC .............. *A61B 7/04* (2013.01); *A61B 5/0205* (2013.01); *A61B 5/0507* (2013.01);
(Continued)

(58) Field of Classification Search
CPC ... A61B 5/0205; A61B 5/0507; A61B 5/1126; A61B 5/7203; A61B 5/7485;
(Continued)

(56) References Cited

U.S. PATENT DOCUMENTS 11,051,702 B2 7/2021 Lin et al.
2012/0302920 A1 11/2012 Bridger et al.
(Continued)

FOREIGN PATENT DOCUMENTS

CN 102715920 B 10/2013

OTHER PUBLICATIONS

Cabot, R.C. et al.,, "Frequency Characteristics of Heart and Lung Sounds," Journal of the American Medical Association, vol. 84, No. 24, Jun. 1925, pp. 1793-1795.
(Continued)

*Primary Examiner* — Robert L Nasser
(74) *Attorney, Agent, or Firm* — Withrow & Terranova, PLLC

(57) ABSTRACT

A radar stethoscope system (12) and method for respiration and heart sound assessment is provided. Embodiments present a method to measure acoustics related to breathing and heartbeat sounds using small-scale radars. Acoustic data derived from the radar return measurements can be based on phase changes of the radar return measurements over a period of time. The radar stethoscope (12) can capture and identify respiratory and heart acoustics as traditionally captured by a clinical stethoscope. Using advanced radar pro-
(Continued)

cessing algorithms, these acoustic signals can be recovered from a distance and without making contact with the patient (14).

16 Claims, 9 Drawing Sheets

(51) Int. Cl.
*A61B 5/0205* (2006.01)
*A61B 5/0507* (2021.01)
*A61B 5/11* (2006.01)
*A61B 7/00* (2006.01)
*G01S 7/03* (2006.01)

(52) U.S. Cl.
CPC .......... *A61B 5/7203* (2013.01); *A61B 5/7485* (2013.01); *G01S 7/03* (2013.01); *A61B 5/1126* (2013.01); *A61B 7/003* (2013.01)

(58) Field of Classification Search
CPC ........... A61B 7/003; A61B 7/00; A61B 7/001; A61B 7/005; A61B 7/006; A61B 7/008; A61B 7/02; A61B 7/023; A61B 7/026; A61B 7/04; A61B 7/045
See application file for complete search history.

(56) References Cited

U.S. PATENT DOCUMENTS

| | | | | |
|---|---|---|---|---|
| 2018/0228468 | A1* | 8/2018 | Adler | A61B 8/5223 |
| 2019/0069840 | A1 | 3/2019 | Young et al. | |
| 2019/0142289 | A1 | 5/2019 | Bliss et al. | |
| 2019/0159960 | A1 | 5/2019 | Nakata et al. | |
| 2021/0000383 | A1* | 1/2021 | Hussain | G01L 19/0654 |
| 2021/0145397 | A1 | 5/2021 | Kim | |
| 2021/0251519 | A1* | 8/2021 | Fitzgibbons | A61B 5/0507 |
| 2021/0345939 | A1 | 11/2021 | Jumbe et al. | |
| 2021/0353156 | A1 | 11/2021 | Rong et al. | |
| 2022/0346653 | A1* | 11/2022 | Teng | A61B 5/0507 |

OTHER PUBLICATIONS

Chowdhury, S.K. et al., “Frequency analysis of adventitious lung sounds,” Journal of Biomedical Engineering, vol. 4, No. 4, Oct. 1982, pp. 305-312.

Forgacs, P.,“Crackles and wheezes,” The Lancet, vol. 290, No. 7508, Jul. 1967, pp. 203-205.

Forgacs, P., “Lung sounds,” British Journal of Diseases of the Chest, vol. 63, No. 1, Jan. 1969, 12 pages.

Lenz, I. et al., “Contactless Stethoscope Enabled by Radar Technology,” Bioengineering, vol. 10, No. 2, Jan. 2023, MDPI, 16 pages.

Lenz, I. et al., “Radarcardiograph Signal Modeling and Time-Frequency Analysis,” 2023 IEEE Radar Conference (RadarConf23), May 1-5, 2023, San Antonio, TX, USA, IEEE, 6 pages.

Rao, A. et al., “Acoustic Methods for Pulmonary Diagnosis,” IEEE Reviews in Biomedical Engineering, vol. 12, Oct. 2018, IEEE, pp. 221-239.

Rong, Y. et al., “Wireless Sensing for Simultaneous Human Vocal Sound and Heart Sound Recognition,” 2023 IEEE International Conference on Acoustics, Speech and Signal Processing (ICASSP), Jun. 4-10, 2023, Rhodes Island, Greece, IEEE, 5 pages.

Sovijärvi, A.R.A. et al., “Standardization of computerized respiratory sound analysis,” European Respiratory Review, vol. 10, No. 77, 2000, p. 585.

Wang, Y. et al., “Abnormal respiratory patterns classifier may contribute to large-scale screening of people infected with covid-19 in an accurate and unobtrusive manner,” arXiv:2002.05534v2 [cs.LG], Dec. 2020, 6 pages.

International Search Report and Written Opinion for International Patent Application No. PCT/US2023/013778, mailed May 17, 2023, 11 pages.

* cited by examiner

RADAR STETHOSCOPE SYSTEM AND METHOD FOR RESPIRATION AND HEART SOUND ASSESSMENT

RELATED APPLICATIONS

This application is a 35 USC 371 national phase filing of International Application No. PCT/US2023/013778, filed Feb. 24, 2023, which claims the benefit of U.S. Provisional Application Ser. No. 63/313,971, filed Feb. 25, 2022, the disclosures of which are incorporated herein by reference in their entireties.

FIELD OF THE DISCLOSURE

The present disclosure relates to non-contact approaches to biometric measurement and assessment, and in particular, using radar signals to determine acoustic data related to vital signs.

BACKGROUND

Traditionally, pulmonary dysfunctions have been diagnosed by analyzing sounds heard through the chest wall, which is referred to as auscultation. The traditional and most convenient method of doing this is by listening to a patient's lung and heart sounds using a stethoscope. When performed by a practiced clinician, this method is generally a good first step in diagnosing a number of pulmonary dysfunctions. However, this method is qualitative, as it is mostly subjective, and thus very error prone.

Other methods can be used in conjunction with auscultation to improve diagnosis and reduce errors. Example methods include spirometry, which focuses on the mechanical characteristics of lung and airway, and fluoroscopy, which utilizes X-Ray imaging. However, spirometry requires cooperation from the patient, thus making it infeasible for newborns and infants. The X-ray imaging required for fluoroscopy can be very costly.

As low-cost acoustic sensors became available it became possible to record and analyze features from recorded signals to provide diagnosis. The spectral characteristics of lung sounds were studied as early as 1925. However, it was not until the late 1960s that various lung sounds were formally categorized as breath sounds and adventitious sounds based on the mechanisms of their production characteristics. Of these categorizations, breath sounds were observed in both normal and abnormal patients, while adventitious sounds were isolated only to the abnormal patients and further classified into sub-groups labeled crackles and wheezes. With these observations, it became feasible to employ computer-based methods for classifying the different sounds and later on, generating accurate diagnoses. Today, there are 162 terms or markers associated with these sounds commonly used in computer respiratory sound analysis (CORSA).

Early studies of lung sounds utilized spectral analysis to associate these sounds to various spectral bands. This, in turn, spawned more studies examining spectral features associated with pulmonary diseases such as asthma, Cryptogenic Fibrosing Alveolitis (CFA), asbestosis, emphysema, pulmonary oedema, and tuberculosis. Modern algorithms employ a combination of advanced signal processing techniques, such as wavelets and the mel-frequency cepstrum, along with machine learning techniques to identify and classify various lung sounds mentioned above. One noted effect of COVID-19 is the presence of rapid breathing, or tachypnea, in potential COVID-19 patients. While COVID-19 effects the respiratory system heavily, it is well documented that the disease can cause heart failure, as well as induce abnormal heart rhythms. These symptoms can be detected using techniques highlighted above.

SUMMARY

A radar stethoscope system and method for respiration and heart sound assessment is provided. Embodiments present a method to measure acoustics related to breathing and heartbeat sounds using small-scale radars. Acoustic data derived from the radar return measurements can be based on phase changes of the radar return measurements over a period of time. The radar stethoscope can capture and identify sounds from respiratory acoustics in respiratory acoustic bands and heart acoustics from heart acoustic bands as traditionally captured by a clinical stethoscope. Using advanced radar processing algorithms, these acoustic signals can be recovered from a distance and without making contact with the patient.

An exemplary embodiment provides a method for implementing a radar stethoscope. The method includes receiving a radar return signal measuring a region of interest of a subject, processing the radar return signal to produce acoustic data corresponding to the region of interest and extracting vital sign acoustic features from the acoustic data.

Another exemplary embodiment provides a radar stethoscope system. The radar stethoscope system includes a radar transceiver and a signal processor coupled to the radar transceiver. The signal processor is configured to cause the radar transceiver to emit a radar signal toward a subject and receive a radar return signal corresponding to the radar signal. The signal processor is further configured to process the radar return signal to produce acoustic data and to extract vital sign acoustic features from the acoustic data.

In another embodiment, a non-transitory computer readable medium comprising computer-readable instructions can be provided. When the instructions are executed by a processor, the processor can perform operations including processing a radar return signal reflected off a skin layer of a region of interest of a patient to generate acoustic data corresponding to the region of interest. The operations can also include extracting vital sign acoustic features from the acoustic data.

In another aspect, any of the foregoing aspects individually or together, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

DETAILED DESCRIPTION

Figure 1:
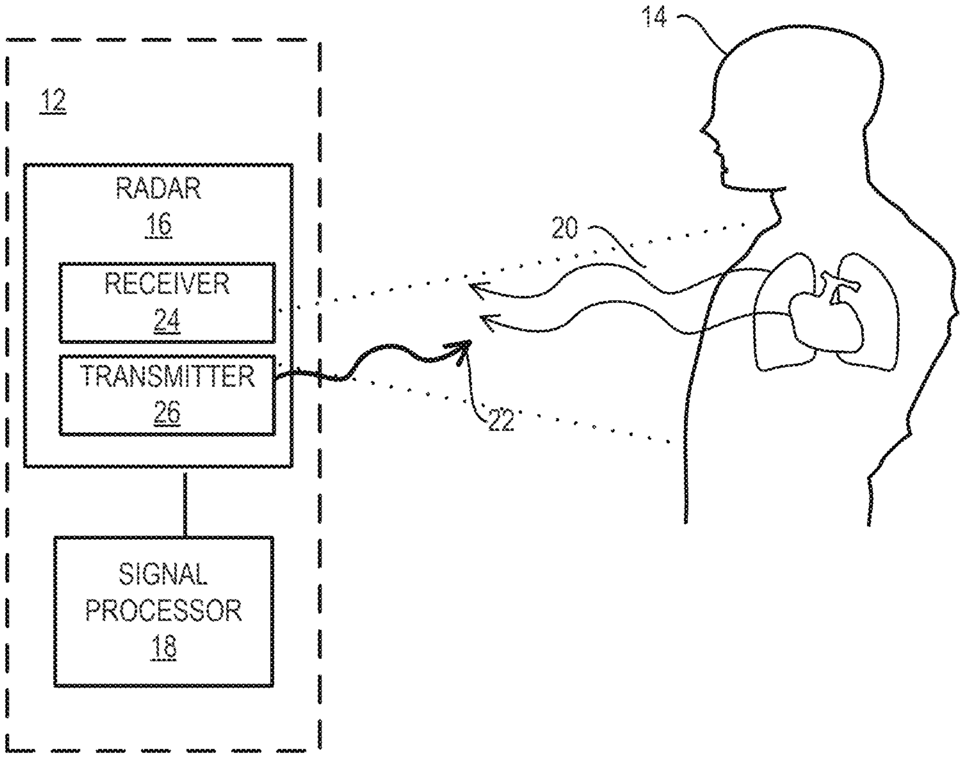
FIG. 1 is a schematic diagram of a radar stethoscope system 12 according to one or more embodiments disclosed herein.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" 20 includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

A radar stethoscope system and method for respiration and heart sound assessment is provided. Embodiments present a method to measure acoustics related to breathing and heartbeat sounds using small-scale radars. Acoustic data derived from the radar return measurements can be based on phase changes of the radar return measurements over a period of time. The radar stethoscope can capture and identify respiratory and heart acoustics as traditionally captured by a clinical stethoscope. Using advanced radar processing algorithms, these acoustic signals can be recovered from a distance and without making contact with the patient.

Acoustic diagnosis utilizing a digital stethoscope (audio reference) suffers from several drawbacks. First, audio noise from external environments, other internal body sounds, or device imperfections can severely degrade the signal and affect diagnosis. One other drawback is that the use of a stethoscope requires cooperation from the subject, which thus makes it even more challenging when trying to examine infants. As a result, achieving good audio signal quality increases the complexity of the algorithms. Embodiments described herein reduce such errors and complexity by extracting vital sign acoustic features from radar signals.

FIG. 1 is a schematic diagram of a radar stethoscope system 12 according to embodiments described herein. The radar stethoscope system 12 provides a non-contact approach to measuring heart, lung, and other acoustic features of the human body of a subject 14. The radar stethoscope system 12 includes a radar sensor 16 (e.g., an ultra-wide band (UWB) radar sensor) to remotely measure acoustic features of vital signs of the subject 14. The radar stethoscope system 12 also includes a signal processor 18 which processes radar signals received by the radar sensor 16 to extract heart acoustic features, lung acoustic features, and multiple vital signs, such as breather rate, heart rate, and so on of the subject 14.

In an exemplary aspect, the radar sensor 16 is coupled to the signal processor 18, which processes a radar return signal 20 received by the radar sensor 16. The radar return signal 20 carries acoustic information corresponding to vital signs of the subject 14, and the signal processor 18 extracts one or more acoustic vital sign features of the subject 14 therefrom.

The radar sensor 16 includes a radar receiver 24 to receive the radar return signal 20 and may further include a radar transmitter 26 which emits a radar signal 22. The radar sensor 16 (via the receiver 24) can receive a radar return signal 20 in any RF band, such as terrestrial radio frequencies, gigahertz (GHz) bands, terahertz bands, microwave bands, etc. The radar return signal 20 can be a reflection of radar signal 22 emitted by the radar transmitter 26 as reflected off the skin of the subject 14. The radar signal 22 may penetrate a portion of the skin of the subject 14 before reflecting back to the radar sensor 16. In some examples, the radar sensor 16 operates on a frequency-modulated continuous-wave (FMCW) signaling scheme with a wide bandwidth in the millimeter or terahertz RF bands. In various embodiments, the radar transmitter 26 can emit the radar signal 22 at predefined intervals over a period of time. The radar receiver 24 can receive a plurality of reflected radar return signals 20, where each radar return signal 20 can correspond to a respective radar signal 22. The signal processor 18 can identify acoustic data by analyzing the radar return signals 20, in particular by processing the radar return signals by comparing phase differences between respective radar return signals 20 which can indicate movement of the subject 14, and in particular, movement caused by vibrations associated with heart sounds or respiratory sounds caused by the lungs or other portion of the subject 14. Based on the frequency band of the radar return signal 20, the amount and frequency of occurrence of the phase differences (indicating magnitude and frequency of acoustic sound) the signal processor 18 can identify acoustic features and vital signs from the radar return signal 20.

In an embodiment, the radar transmitter 26 can transmit the radar signals 22 at predefined frequencies and/or bands based on the type of vital sign desired to be extracted. The radar transmitter 26 can also alternate the frequency and/or band according to some predefined pattern (e.g., sequentially) to capture acoustic data associated with different sources.

Figure 2:
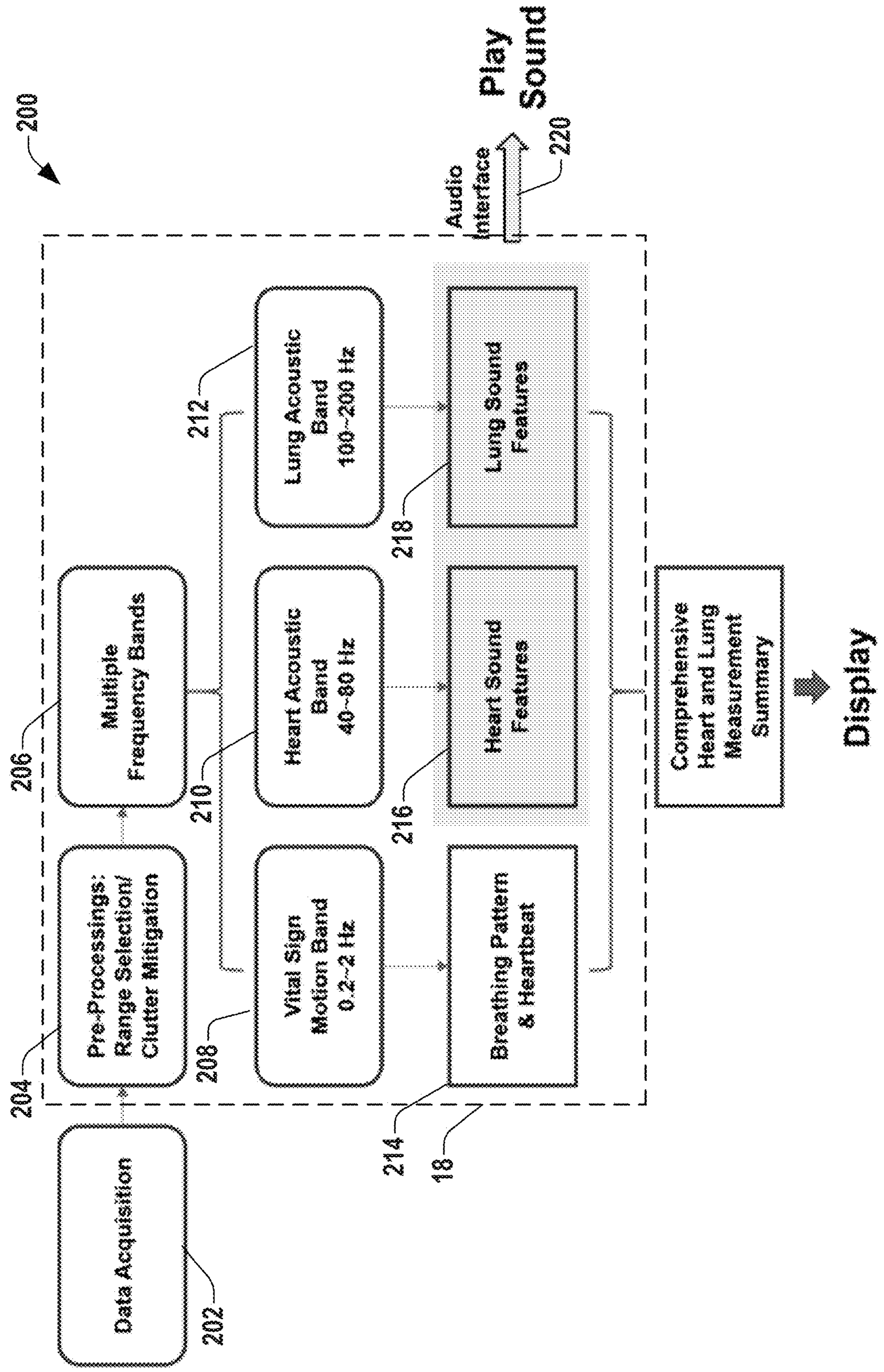
FIG. 2 is a block diagram illustrating a processing chain to extract heart and lung acoustic features according to one or more embodiments disclosed herein.

FIG. 2 is a block diagram illustrating a processing chain 200 of the signal processor 18 to extract heart and respiratory acoustic features according to embodiments described herein. After data acquisition at 202 (e.g., by the radar receiver 24) initial pre-processing of the raw data at 204, which includes range selection and clutter mitigation, embodiments look at the energy distribution at various frequency ranges of interest at 206. In an exemplary aspect, these frequency ranges of interest include 1) a vital sign motion band 208, which may range from 0.2 hertz (Hz) to 2 Hz which can help identify breathing patterns and heartbeat at 214; 2) a heart acoustic band 210, which may range from 40 Hz to 80 Hz and which can identify heart sound features at 216; 3) a lung acoustic band 212 (associated with respiratory sounds), which may range from 100 Hz to 200 Hz and can be used to identify lung sounds features (e.g., adventitious sounds) at 218. In some embodiments, the acoustic data can range from 20 Hz and 8000 Hz.

For evaluation, the radar acoustic features are validated by correlating them with acoustic features measured by a traditional stethoscope. In an embodiment, an audio interface can be provided at 220 to generating an acoustic signal comprising the acoustic features identified in the signal processor and provide or transmit the acoustic signal to a speaker to generate sounds based on the acoustic signal.

In an embodiment, the radar stethoscope system 12 can be a FMCW radar system using a sawtooth waveform as the transmitting signal is utilized. The signal is analytically expressed as:

$$s_{Tx}(\tau, t) = \exp\{2\pi f_0 \tau + \pi\alpha\tau^2\}, \quad \text{Eqn. 1}$$

where $\alpha = B/T_c$ is the slope rate of the frequency sweep, $f_0$ is the starting frequency, $\tau$ is the fast time $\in [0T_c]$, and t is the slow time. The backscattered at the radar receiver for one chirp frame is expressed as:

$$s_{Rx} = A(t) s_{Tx}\left(\tau - 2\frac{d(t)}{c}\right), \quad \text{Eqn. 2}$$

where d(t) is the time-varying physical displacement and A(t) is a complex amplitude, encapsulating the channel effects and target response. Usually, the signal processing is done after mixer in complex baseband. For MIMO FMCW radar with multiple Tx and Rx antennas under far-field assumption, the time delay among the array elements is simplified as a phase difference along the incident angle in the baseband signal. For a uniform linear virtual array, the baseband signal of MIMO FMCW radar at the $i^{th}$ element is expressed as:

$$s_{Rx,i}(\tau, t) = A(t)\exp\left\{j\left(\frac{4\pi\alpha d(t)\tau}{c} + \frac{4\pi f_0 d(t)}{c}\right)\right\} \times \exp\left\{j\frac{2\pi d}{\lambda}(i-1)\sin(\theta)\right\} \quad \text{Eqn. 3}$$

where θ is the incident angle and d is the antenna spacing. The body displacements is extracted in the phase of the beat signal.

A multi-beam operation is applied to isolate the desired target at the incident angle θ from other targets located at different angles. By combining multiple spatial channels, the signal quality is improved. The beam-steering vector w is given as:

$$w = \left[1 e^{-j\frac{2\pi d}{\lambda}sin(\theta)} e^{-j\frac{2\pi d}{\lambda}2sin(\theta)}, \ldots, e^{-j\frac{2\pi d}{\lambda}(N-1)sin(\theta)}\right]^T \quad \text{Eqn. 4}$$

where N is the size of the MIMO virtual array. The output of the virtual array is:

$$s = [s_1 s_1, \ldots, s_N]^T \quad \text{Eqn. 5}$$

The beamformer output is given by the inner product of Eqn. (4) and Eqn. (5), $$y(\tau, t) = w^T \cdot s = NA(t) \times \exp\left\{j\left[\frac{4\pi\alpha d(t)\tau}{c}\right] + \frac{4\pi f_0 d(t)}{c}\right\}. \quad \text{Eqn. 6}$$

The modulated phase of the beat signal contains the signal of interest. Fast-time FFT is first invoked over each chirp frame. The FFT results of Eqn. (6) is expressed as:

$$S(v, t) = TNA(t)\exp\left\{j\frac{4\pi f_0 d(t)}{c}\right\} \cdot \text{sinc}\left\{\frac{2\alpha}{c}[v - v_T]\right\}, \quad \text{Eqn. 7}$$

where v, representing range profile, is the Fourier component with respect to τ. The maximum signal response is obtained at the target range bin, $v_T$. Eqn. (7) is then simplified as, $$S(v, t) = TNA(t)\exp\left\{j\frac{4\pi f_0 d(t)}{c}\right\}. \quad \text{Eqn. 8}$$

The phase variation due to human vocal motion and chest motion can be estimated from Eqn. 8.

Figure 3:
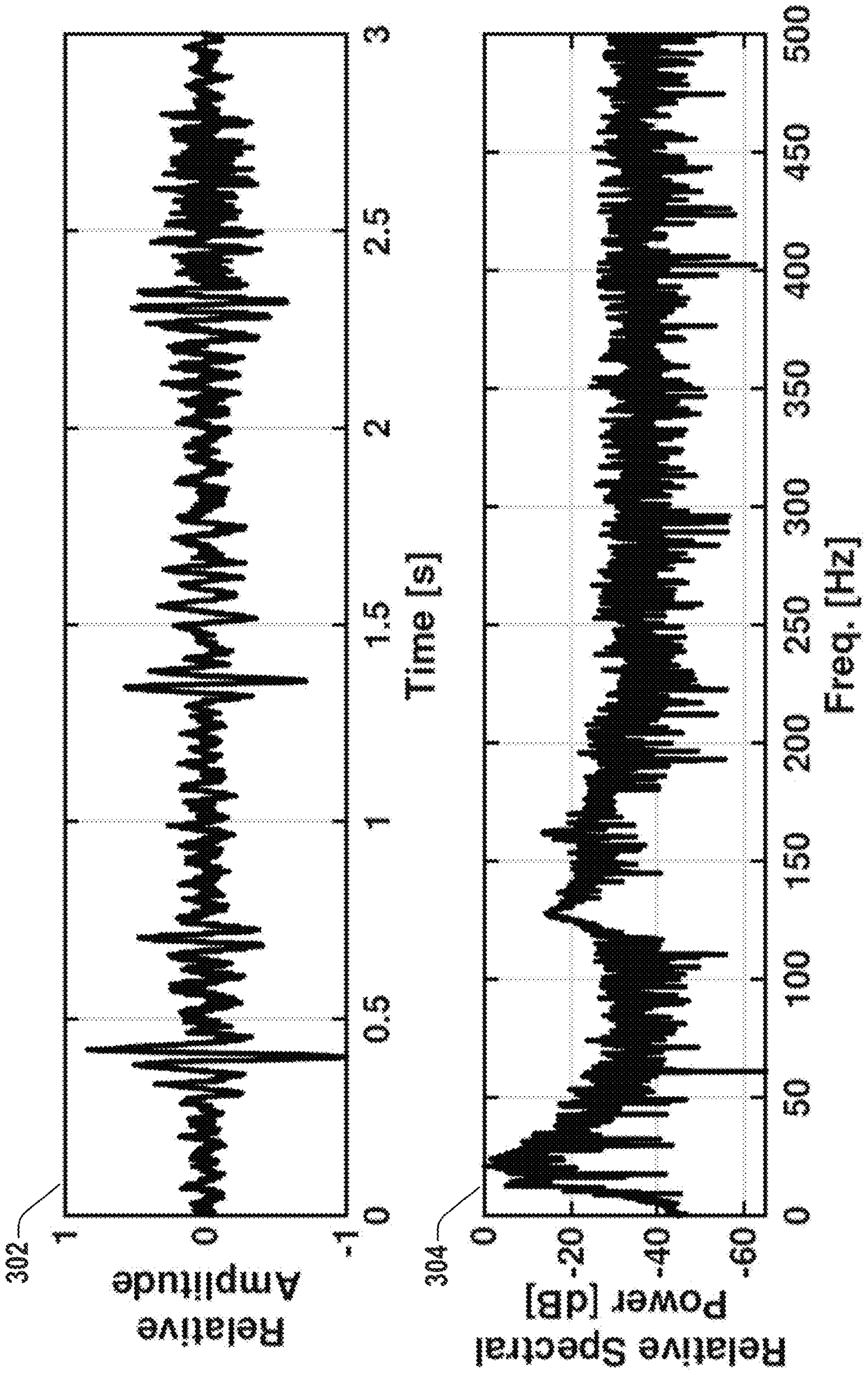
FIG. 3 is a signal waveform and spectrum consisting of radar vocal sound and radar heart sound according to one or more embodiments disclosed herein.

Signal waveform analysis and frequency analysis are generally useful tools. However, when the analyzed signal is composited of two types of signals, such as vocal sound and heart sound, it is challenging to identify their signatures and separate them subsequently. In specifically, one measurement example for 3 seconds is displayed in graph 302 of FIG. 3. The test subject was enunciating 'I am a boy' and sitting still on a chair. The mixed signals hardly show any signs of vocal sound in FIG. 2 (top). Distorted heart sound events occur at 0.38, 1.26 and 2.31 seconds. The corresponding spectrum in graph 304 shows two major spectral peak.

Like many other natural signals, physiological signals are time-varying and non-stationary. In this study, time frequency analysis is implemented using short-time-Fourier-Transform (STFT) to reveal meaningful time-varying signatures. The STFT is defined as:

$$P(\tau, \omega) = \int_{-\infty}^{\infty} p(t)w(t-\tau)e^{-i\omega t}dt, \quad \text{Eqn. 9}$$

Where p(t) is the extracted phase signal and w(t) is a non-zero window function. The window length has to approximately match the time scale of the analyzed signal.

The STFT spectrogram from the same data exhibits the distinctive spectral features of the radar vocal sound and radar heart sound. Energy clusters below 100 Hz are mainly related to heart sound while the ones above 100 Hz are mainly related to vocal sound. Radar heart sound signal power is about 15 dB stronger than that of radar vocal sound. Additionally, the instantaneous frequency of the two signals behave differently with time. Radar heart sound shows up as a train of bursts that are low in frequency and short in time. On the other hand, radar vocal sound is relatively high in frequency and expanded in time. Based on this observation, radar vocal sound and radar heart sound can be separated through spectral filtering for enhanced identification.

Figure 4:
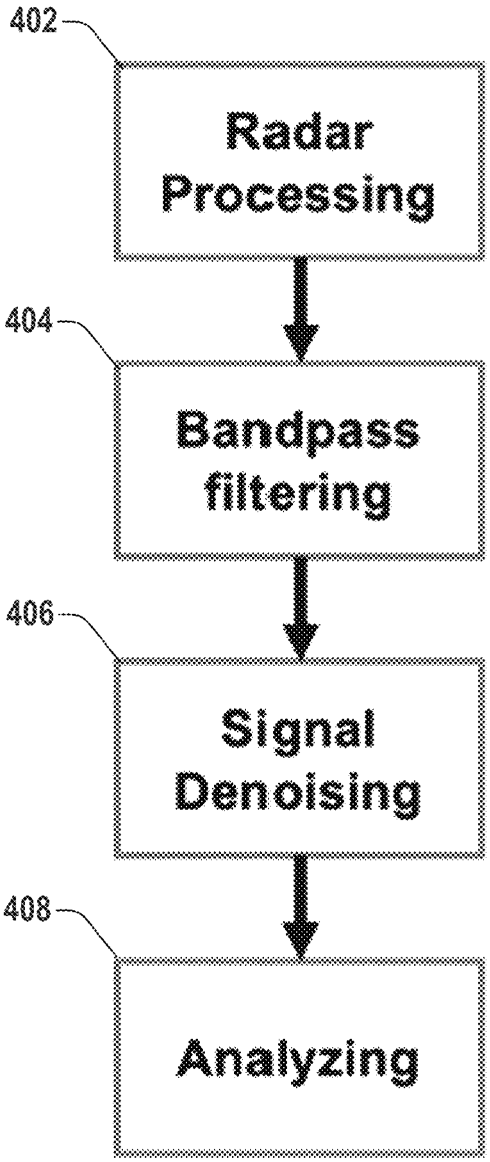
FIG. 4 is a high-level signal processing chain for signal enhancement according to one or more embodiments disclosed herein.

The high-level signal processing chain for signal enhancement is summarized in FIG. 4. Radar processing 402 includes subject detection, beamforming, range FFT and phase extraction. Bandpass filtering 404 is applied to separate radar vocal sound and heart sound based on their spectral signatures. A wavelet based denoising algorithm 406 is implemented using 1-D discrete stationary wavelet transform (SWT) with a soft thresholding for denoising. The SWT decomposition during the analysis phase 408 of the filtered radar signals is results in a denoised radar vocal sound and radar heart sound have an enhanced signal quality. The developed signal processing chain improves the radar vocal sound signal to noise ratio (SNR) and thus the traces of the 2nd and 3rd-order harmonics of the fundamental vocal sound are recovered in the spectrogram. Similarly, the SNR improvement is found in the denoised radar heart sound.

Figure 5A:
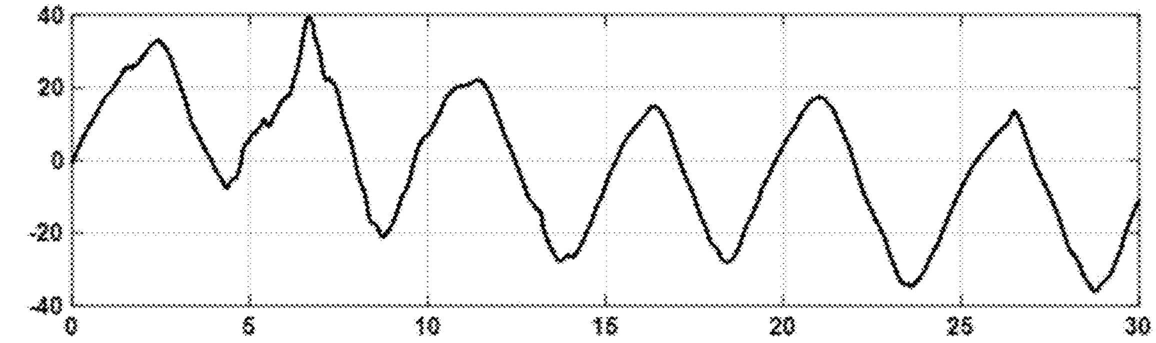
FIG. 5A is a graphical representation of a measured breathing pattern according to one or more embodiments disclosed herein.
Figure 5B:
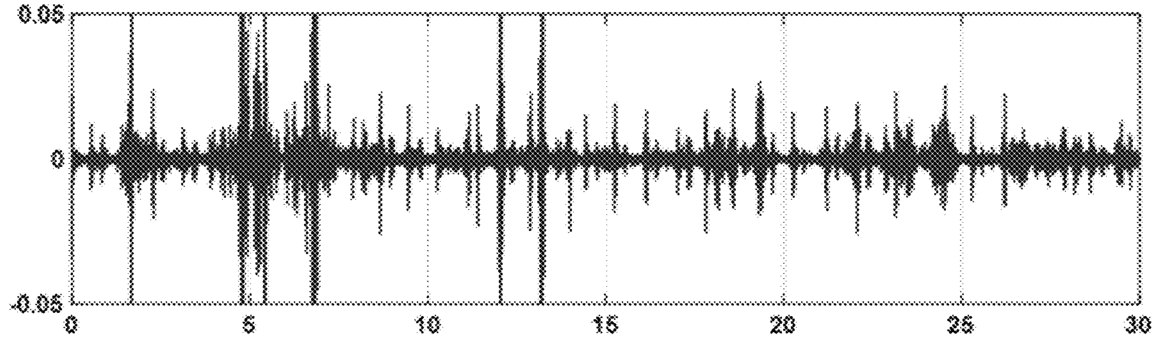
FIG. 5B is a graphical representation of a measured heart sound signal after applying a bandpass filter at 20-100 hertz (Hz) according to one or more embodiments disclosed herein.
Figure 5C:
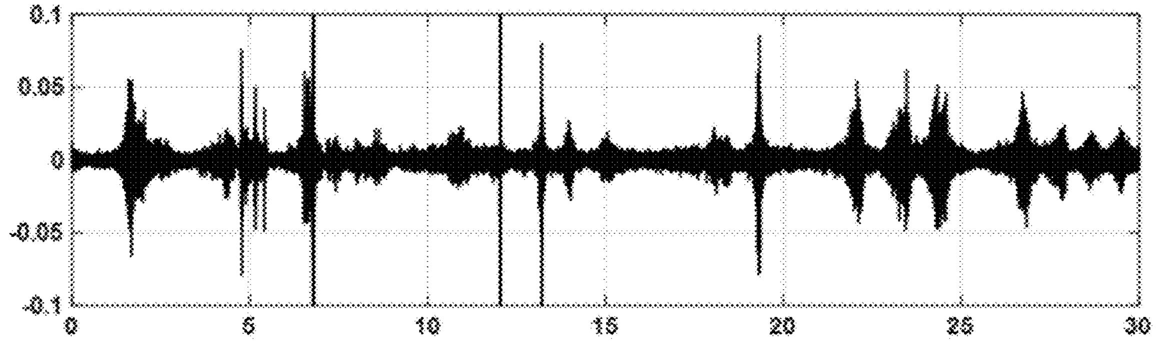
FIG. 5C is a graphical representation of the breathing sound signal after applying a bandbass filter at 100-1500 Hz according to one or more embodiments disclosed herein.
Figure 5D:
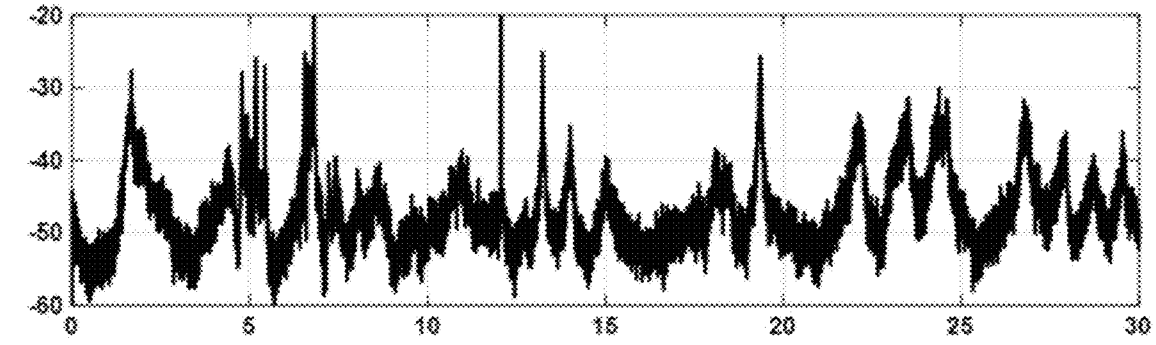
FIG. 5D is a graphical representation of energy of the breathing sound signal after smoothing the absolute value of the breathing sound signal in FIG. 3 according to one or more embodiments disclosed herein.

FIG. 5A is a graphical representation of a measured breathing pattern. FIG. 5B is a graphical representation of a measured heart sound signal after applying a bandpass filter at 20-100 hertz (Hz) FIG. 5C is a graphical representation of the breathing sound signal after applying a bandpass filter at 100-1500 Hz. FIG. 5D is a graphical representation of energy of the breathing sound signal after smoothing the absolute value of the breathing sound signal in FIG. 5C.

Figure 6:
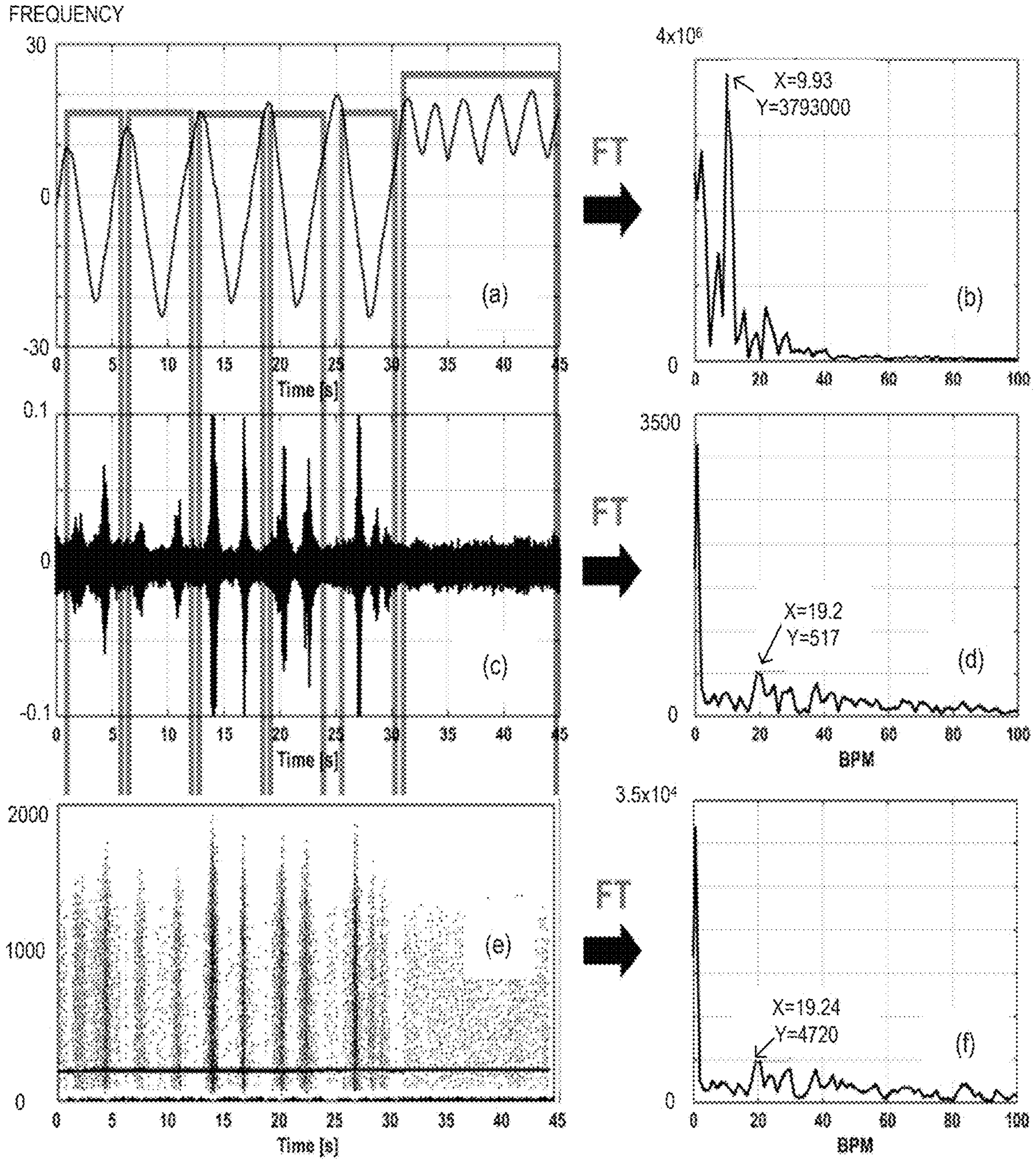
FIG. 6 is a graphical representation of an initial analysis comparing the filtered radar signal from the breathing sound frequency band with the actual breathing pattern according to one or more embodiments disclosed herein.

FIG. 6 is a graphical representation of an initial analysis comparing the filtered radar signal from the breathing sound frequency band with the actual breathing pattern. Embodiments of the present disclosure are able to trace meaningful vital sign information by comparing with the breathing motion pattern and filtered signal at the breathing sound frequency band both extracted from radar measurements.

Figure 7:
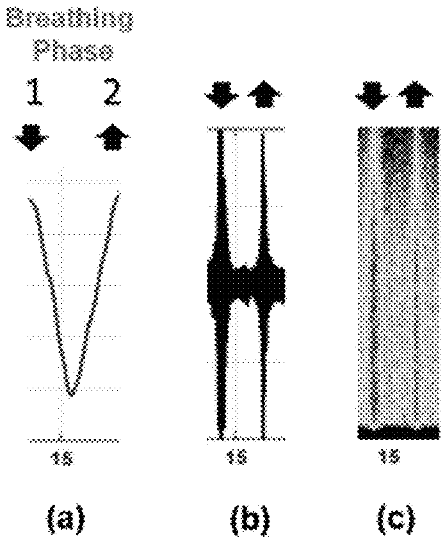
FIG. 7 is a graphical representation illustrating breathing phase detection from the radar lung acoustic band signal according to one or more embodiments disclosed herein.

FIG. 7 is a graphical representation illustrating breathing phase detection from the radar lung acoustic band signal. Embodiments can detect the breathing phases and various acoustic features embedded in those phases from the time-frequency representation of the signal.

The proposed radar stethoscope system is able to extract multiple vital signs including, breathing rate, heart rate, lung acoustics and heart acoustics, using high frequency UWB radar. No current devices have such capabilities.

Figure 8:
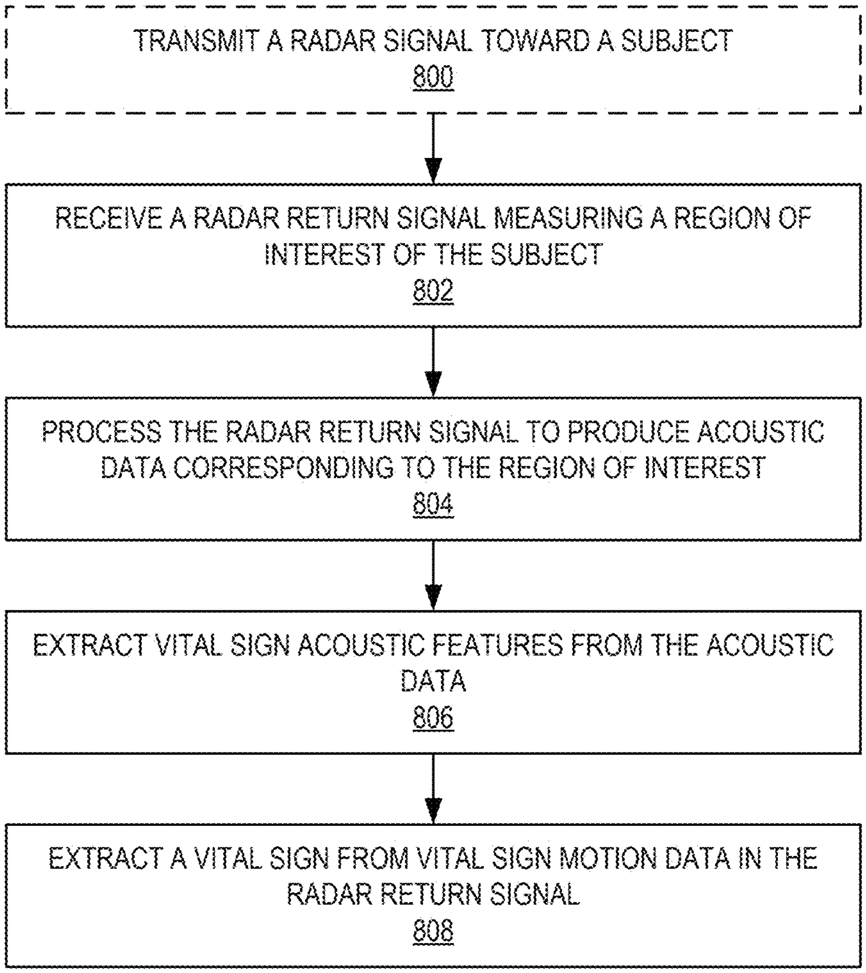
FIG. 8 is a flow diagram illustrating a process for implementing a radar stethoscope according to one or more embodiments disclosed herein.

FIG. 8 is a flow diagram illustrating a process for implementing a radar stethoscope. Dashed boxes represent optional steps. The process may optionally begin at operation 800, with transmitting a radar signal toward a subject. In an exemplary aspect, the radar signal is a UWB radar signal. The process continues at operation 802, with receiving a radar return signal measuring a region of interest of the subject. The process continues at operation 804, with processing the radar return signal to produce acoustic data corresponding to the region of interest. In an exemplary aspect, processing the radar return signal includes selecting a signal range corresponding to the region of interest and/or removing background noise from the radar return signal.

The process continues at operation 806, with extracting vital sign acoustic features from the acoustic data. In an exemplary aspect, the acoustic data comprises acoustic data in a heart acoustic band and a lung acoustic band. extracting vital sign acoustic features can include extracting heart sound features from the heart acoustic band and lung sound features form the lung acoustic band. The process may optionally continue at operation 808, with extracting a vital sign from vital sign motion data in the radar return signal.

Although the operations of FIG. 8 are illustrated in a series, this is for illustrative purposes and the operations are not necessarily order dependent. Some operations may be performed in a different order than that presented. Further, processes within the scope of this disclosure may include fewer or more steps than those illustrated in FIG. 8.

Figure 9:
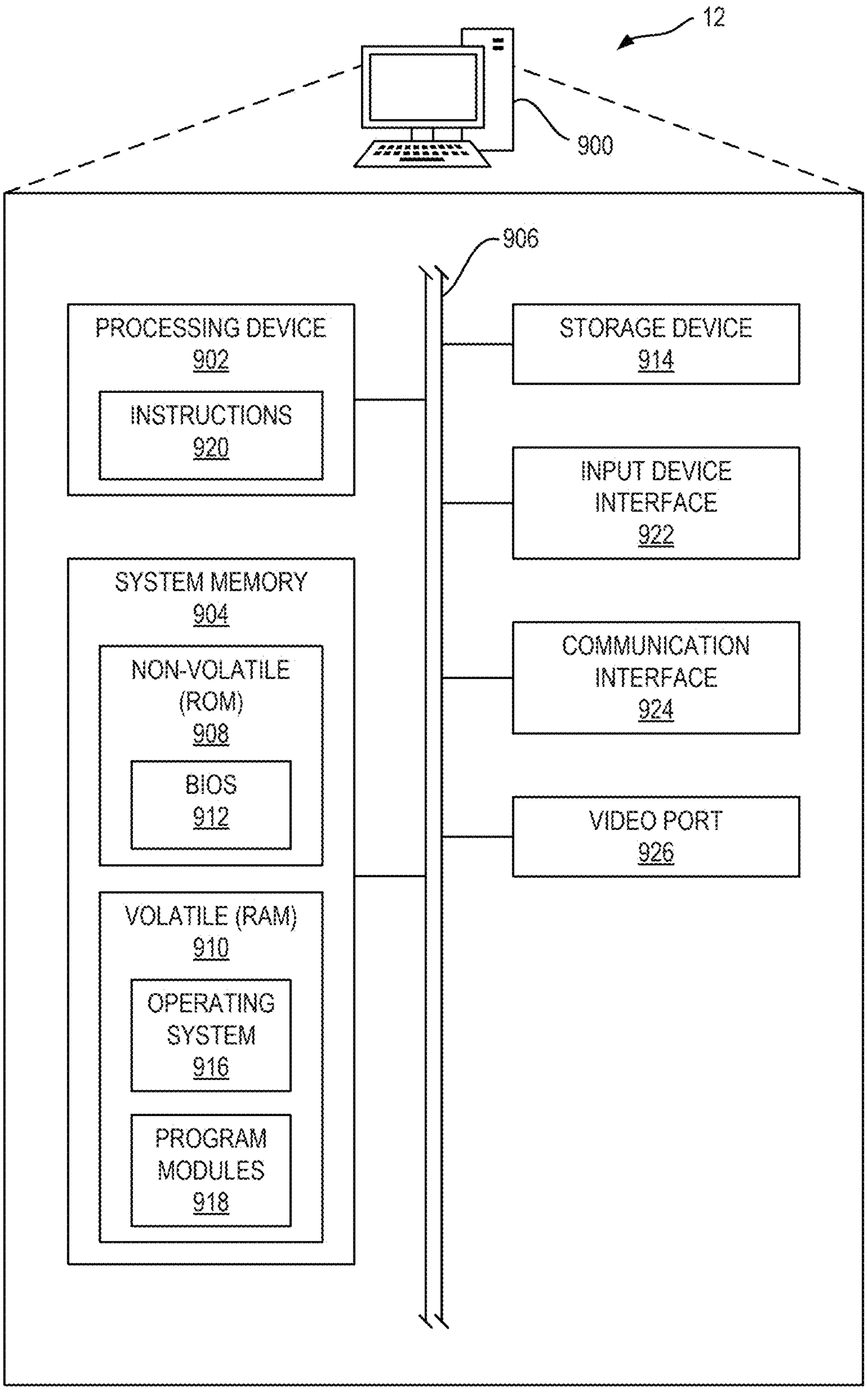
FIG. 9 is a block diagram of the radar stethoscope system according to embodiments disclosed herein.

FIG. 9 is a block diagram of the radar stethoscope system 10 according to embodiments disclosed herein. The radar stethoscope system 10 includes or is implemented as a computer system 900, which comprises any computing or electronic device capable of including firmware, hardware, and/or executing software instructions that could be used to perform any of the methods or functions described above. In this regard, the computer system 900 may be a circuit or circuits included in an electronic board card, such as a printed circuit board (PCB), a server, a personal computer, a desktop computer, a laptop computer, an array of computers, a personal digital assistant (PDA), a computing pad, a mobile device, or any other device, and may represent, for example, a server or a user's computer.

The exemplary computer system 900 in this embodiment includes a processing device 902 or processor, a system memory 904, and a system bus 906. The processing device 902 represents one or more commercially available or proprietary general-purpose processing devices, such as a microprocessor, central processing unit (CPU), or the like. More particularly, the processing device 902 may be a complex instruction set computing (CISC) microprocessor, a reduced instruction set computing (RISC) microprocessor, a very long instruction word (VLIW) microprocessor, a processor implementing other instruction sets, or other processors implementing a combination of instruction sets. The processing device 902 is configured to execute processing logic instructions for performing the operations and steps discussed herein.

In this regard, the various illustrative logical blocks, modules, and circuits described in connection with the embodiments disclosed herein may be implemented or performed with the processing device 902, which may be a microprocessor, field programmable gate array (FPGA), a digital signal processor (DSP), an application-specific integrated circuit (ASIC), or other programmable logic device, a discrete gate or transistor logic, discrete hardware components, or any combination thereof designed to perform the functions described herein. Furthermore, the processing device 902 may be a microprocessor, or may be any conventional processor, controller, microcontroller, or state machine. The processing device 902 may also be implemented as a combination of computing devices (e.g., a combination of a DSP and a microprocessor, a plurality of microprocessors, one or more microprocessors in conjunction with a DSP core, or any other such configuration).

The system memory 904 may include non-volatile memory 908 and volatile memory 910. The non-volatile memory 908 may include read-only memory (ROM), erasable programmable read-only memory (EPROM), electrically erasable programmable read-only memory (EEPROM), and the like. The volatile memory 910 generally includes random-access memory (RAM) (e.g., dynamic random-access memory (DRAM), such as synchronous DRAM (SDRAM)). A basic input/output system (BIOS) 912 may be stored in the non-volatile memory 908 and can include the basic routines that help to transfer information between elements within the computer system 900.

The system bus 906 provides an interface for system components including, but not limited to, the system memory 904 and the processing device 902. The system bus 906 may be any of several types of bus structures that may further interconnect to a memory bus (with or without a memory controller), a peripheral bus, and/or a local bus using any of a variety of commercially available bus architectures.

The computer system 900 may further include or be coupled to a non-transitory computer-readable storage medium, such as a storage device 914, which may represent an internal or external hard disk drive (HDD), flash memory, or the like. The storage device 914 and other drives associated with computer-readable media and computer-usable media may provide non-volatile storage of data, data structures, computer-executable instructions, and the like. Although the description of computer-readable media above refers to an HDD, it should be appreciated that other types of media that are readable by a computer, such as optical disks, magnetic cassettes, flash memory cards, cartridges, and the like, may also be used in the operating environment, and, further, that any such media may contain computer-executable instructions for performing novel methods of the disclosed embodiments.

An operating system 916 and any number of program modules 918 or other applications can be stored in the volatile memory 910, wherein the program modules 918 represent a wide array of computer-executable instructions corresponding to programs, applications, functions, and the like that may implement the functionality described herein in whole or in part, such as through instructions 920 on the processing device 902. The program modules 918 may also reside on the storage mechanism provided by the storage device 914. As such, all or a portion of the functionality described herein may be implemented as a computer program product stored on a transitory or non-transitory computer-usable or computer-readable storage medium, such as the storage device 914, volatile memory 910, non-volatile memory 908, instructions 920, and the like. The computer program product includes complex programming instructions, such as complex computer-readable program code, to cause the processing device 902 to carry out the steps necessary to implement the functions described herein.

An operator, such as the user, may also be able to enter one or more configuration commands to the computer system 900 through a keyboard, a pointing device such as a mouse, or a touch-sensitive surface, such as the display device, via an input device interface 922 or remotely through a web interface, terminal program, or the like via a communication interface 924. The communication interface 924 may be wired or wireless and facilitate communications with any number of devices via a communications network in a direct or indirect fashion. An output device, such as a display device, can be coupled to the system bus 906 and driven by a video port 926. Additional inputs and outputs to the computer system 900 may be provided through the system bus 906 as appropriate to implement embodiments described herein.

In one or more embodiments, a method for remote vital sign assessment can be provided, where the method comprises receiving a radar return signal measuring a region of interest of a subject. The method can also include processing the radar return signal to produce acoustic data corresponding to the region of interest. The method can also include extracting vital sign acoustic features from the acoustic data.

In an embodiment, the radar return signal is received in response to transmitting a radar signal from a single radar emitter.

In an embodiment, the radar signal comprises a wideband millimeter or terahertz radio frequency (RF) signal.

In an embodiment, processing the radar return signal comprises selecting a signal range corresponding to the region of interest.

In an embodiment, processing the radar return signal further comprises removing background noise from the radar return signal.

In an embodiment, the acoustic data comprises acoustic data in a heart acoustic band and a lung acoustic band.

In an embodiment, the heart acoustic band comprise frequencies between 20 Hz and 100 Hz and the lung acoustic band comprises frequencies between 80 Hz and 2000 Hz.

In an embodiment, the heart acoustic band comprise frequencies between 40 Hz and 80 Hz and the lung acoustic band comprises frequencies between 100 Hz and 200 Hz.

In an embodiment, extracting the vital sign acoustic features from the acoustic data comprises extracting heart sound features from the heart acoustic band and lung sound features form the lung acoustic band.

In an embodiment, the radar return signal further comprises a vital sign motion data in a vital sign motion band.

In an embodiment, the vital sign motion band comprises frequencies between 0.1 Hz and 3 Hz.

In an embodiment, the vital sign motion band comprises frequencies between 0.2 Hz and 2 Hz.

In an embodiment, the method can include extracting a vital sign from the vital sign motion data in the vital sign motion band.

In an embodiment, a vital sign assessment system can be provided. The vital sign assessment system can include a radar transceiver and a signal processor coupled to the radar transceiver. In an embodiment, the vital sign assessment system can emit a radar signal toward a subject. In an embodiment, the vital sign assessment system can receive a radar return signal corresponding to the radar signal. In an embodiment, the vital sign assessment system can extract vital sign acoustic features from the acoustic data.

In an embodiment, the vital sign acoustic features comprise at least one of heart acoustic features or lung acoustic features.

In an embodiment, the vital signal assessment system can also comprise a radar emitter configured to emit a wideband millimeter or terahertz RF signal toward the subject.

The operational steps described in any of the exemplary embodiments herein are described to provide examples and discussion. The operations described may be performed in numerous different sequences other than the illustrated sequences. Furthermore, operations described in a single operational step may actually be performed in a number of different steps. Additionally, one or more operational steps discussed in the exemplary embodiments may be combined.

Those skilled in the art will recognize improvements and modifications to the preferred embodiments of the present disclosure. All such improvements and modifications are considered within the scope of the concepts disclosed herein and the claims that follow.

What is claimed is:

1. A method for implementing a radar stethoscope, the method comprising:

receiving a radar return signal measuring a region of interest of a subject;

processing the radar return signal to produce acoustic data corresponding to the region of interest, wherein the acoustic data is based on phase differences of the radar return signal over a period of time;

extracting vital sign acoustic features from the acoustic data;

generating an acoustic signal comprising the vital sign acoustic features; and transmitting the acoustic signal to a speaker to generate sound based on the acoustic signal.

2. The method of claim 1, wherein the radar return signal is received in response to transmitting a radar signal from a single radar emitter.

3. The method of claim 2, wherein the radar signal comprises a wideband millimeter or terahertz radio frequency (RF) signal.

4. The method of claim 1, wherein processing the radar return signal comprises selecting a signal range corresponding to the region of interest.

5. The method of claim 4, wherein processing the radar return signal further comprises removing background noise from the radar return signal.

6. The method of claim 5, wherein the acoustic data comprises acoustic data between 20 Hz and 8000 Hz.

7. The method of claim 5, wherein the radar return signal further comprises a vital sign motion data in a vital sign motion band.

8. The method of claim 7, wherein the vital sign motion band comprises frequencies between 0.1 Hz and 3 Hz.

9. The method of claim 7, wherein the vital sign motion band comprises frequencies between 0.2 Hz and 2 Hz.

10. The method of claim 7, further comprising:

extracting a vital sign from the vital sign motion data in the vital sign motion band.

11. The method of claim 1, wherein the acoustic data comprises acoustic data in a heart acoustic band and a respiratory acoustic band.

12. The method of claim 11, wherein:

the heart acoustic band comprises frequencies between 20 Hz and 100 Hz; and the respiratory acoustic band comprises frequencies between 80 Hz and 2000 Hz.

13. The method of claim 11, wherein extracting the vital sign acoustic features from the acoustic data comprises extracting heart sound features from the heart acoustic band and respiratory sound features from the respiratory acoustic band.

14. A radar stethoscope system, comprising:

a radar transceiver; and a signal processor coupled to the radar transceiver and configured to:

cause the radar transceiver to emit a radar signal toward a subject;

receive a radar return signal corresponding to the radar signal;

process the radar return signal to produce acoustic data, wherein the acoustic data is based on phase differences of the radar return signal over a period of time;

extract vital sign acoustic features from the acoustic data;

generate an acoustic signal comprising the vital sign acoustic features; and transmit the acoustic signal to a speaker to generate sound based on the acoustic signal.

15. The radar stethoscope system of claim 14, wherein the radar transceiver emits a wideband millimeter or terahertz RF signal toward the subject.

16. A non-transitory computer readable medium comprising computer-readable instructions, that when executed by a processor, cause the processor to perform operations, the operations comprising:

processing a radar return signal reflected off a skin layer of a region of interest of a patient to generate acoustic data corresponding to the region of interest, wherein the acoustic data is based on phase differences of the radar return signal over a period of time;

extracting vital sign acoustic features from the acoustic data;

generating an acoustic signal comprising the vital sign acoustic features; and transmitting the acoustic signal to a speaker to generate sound based on the acoustic signal.

* * * * *